US005384122A

United States Patent [19]

Cunningham et al.

[11] Patent Number: 5,384,122

[45] Date of Patent: Jan. 24, 1995

[54] HERPESVIRUS PARTICLES AND VACCINE

[75] Inventors: Charles Cunningham, Kirkintilloch; John McLauchlan, Bishopbriggs; Frazer J. Rixon, Strathblane; Jozsef F. Szilagyi, Uddingston, all of Scotland

[73] Assignee: Medical Research Council, London, England

[21] Appl. No.: 95,041

[22] Filed: Jul. 22, 1993

Related U.S. Application Data

[63] Continuation of Ser. No. 843,171, Feb. 28, 1992, abandoned.

[30] Foreign Application Priority Data

May 7, 1991 [GB] United Kingdom ................ 9109763
Jul. 8, 1991 [GB] United Kingdom ................ 9114714

[51] Int. Cl.$^6$ ........................ A61K 39/12; C12N 7/04; C12N 15/00; C07K 3/00

[52] U.S. Cl. ................................ 424/231.1; 530/350; 435/172.1; 435/235.1

[58] Field of Search .......................... 530/350; 424/89; 435/235.1, 172.1

[56] References Cited

U.S. PATENT DOCUMENTS 4,999,296 3/1991 Kit et al. ......................... 435/235.1

OTHER PUBLICATIONS

Shih et al "Expression of Heptitis B. virus . . . " Proc. Natl Acad. Sci. USA, vol. 81, 1984, pp. 5867–5870.

Szilagyi et al, 1991, J. Gen. Virol. 72:661–668.

Preston, et al., 1093, "Identification and Characterization of a herpes . . . " J. of Virology 45(3):1056–1064.

Willey, et al., 1988, "In Vitro Mutagenesis Identifies a Region . . . " J. of Virology 63z;139–147.

Irmiere, et al., 1983, "Isolation and Characterization of . . . " Virology 130–118–133.

*Primary Examiner*—Christine M. Nucker
*Assistant Examiner*—Lynette F. Smith
*Attorney, Agent, or Firm*—Nixon & Vanderhye

[57] ABSTRACT

In addition to virions, herpesvirus-infected cells produce non-infectious particles, termed L-particles, which consist of tegument surrounded by envelope but lack the nucleocapsid. L-particles of a herpesvirus can be prepared substantially free of infectious virions, e.g. by allowing an appropriate temperature-sensitive mutant to replicate at its non-permissive temperature, and such L-particles are useful as a component of a vaccine against the herpesvirus. They can also be prepared to contain a foreign protein or peptide, by use of a recombinant herpesvirus.

17 Claims, 2 Drawing Sheets

HERPESVIRUS PARTICLES AND VACCINE

This application is a continuing application from application Ser. No. 07/843,171 filed Feb. 28, 1992, now abandoned.

BACKGROUND OF THE INVENTION

1. Field of the Invention

The invention relates to a form of herpesvirus particle for use in vaccination and to vaccines containing it.

2. Description of the Related Art

In infectious virions of herpes simplex virus, the virus DNA is contained in an icosahedral nucleocapsid that is in turn enclosed by an amorphous proteinaceous tegument and a glycoprotein-containing envelope (Dargan, 1986).

SUMMARY OF THE INVENTION

During purification of a strain of herpes simplex virus type 1 (HSV-1) by velocity gradient centrifugation, two distinct particle bands were observed. In addition to the virion band, there was a band of lighter particles above it. These consist of tegument surrounded by an envelope but lack the viral capsid and DNA, and consequently are non-infectious. They have been termed "L-particles". We have found that L-particles are also produced by another strain of HSV-1 and by other herpesviruses.

The appearance and composition of L-particles suggest that their genesis is related to that of virions although differences in the compositions of the two types of particle indicate that their pathways of assembly are not identical. L-particles offer potential for a non-infectious subunit vaccine but inability to produce them substantially free from contaminating virions is an obstacle.

We have examined the production of virus-related particles using ts 1201, a temperature-sensitive mutant of HSV-1 with a defect in gene UL26 (Preston et al., 1983, Preston et al., 1991). At non-permissive temperatures, ts 1201 makes viral DNA and a full spectrum of viral proteins including the late structural species. Capsid assembly takes place at these temperatures but viral DNA is not packaged and the immature capsids are retained in the nucleus (Preston et al., 1983). Thus, mature virions are not produced at the non-permissive temperature. We have shown that the mutant ts 1201 produces L-particles at the non-permissive temperature in quantities similar to those generated by wild type virus. The ability of this mutant to assemble L-particles shows that their formation can take place without the involvement of capsids. Thus, for ts 1201, and by inference for other mutants of wild type virus also, assembly of L-particles can be made independent of virion assembly, making it possible to isolate L-particles substantially free of contaminating virions and thereby enable their use as the active ingredient of a vaccine.

In view of the above findings, the present invention provides virion-like, but non-infectious, L-particles of a herpesvirus, comprising tegument surrounded by an envelope, but which lack a capsid and the viral DNA within the capsid, both per se and for use in vaccination against herpesvirus infections.

The term "L-particles", as used herein, is not to be construed as indicative of any particular method used to produce them, but, rather, as a convenient label by which to refer to the particles defined above. Although they have been produced from a wild type virus and from a temperature-sensitive mutant, it will be appreciated that they will more conveniently be obtainable by recombinant DNA means. The findings explained herein indicate that by disabling the processes and signals responsible for the formation or release from the nucleus of a nucleocapsid structure it will be possible to produce L-particles substantially free of infectious virions.

By using a recombinant herpesvirus containing DNA encoding a foreign protein or peptide, the L-particles can be prepared to contain such a foreign protein or peptide, thus enabling them to be used in combatting other diseases than herpesvirus infections.

The invention also includes vaccine containing L-particles of a herpesvirus. The vaccine can contain a vehicle or an immunostimulating agent such as an adjuvant.

The invention includes a method vaccination, against a disease, of a mammal infectable by a herpesvirus, which comprises administering to said mammal an immunologically effective amount of L-particles of the invention, said L-particles containing a peptide or protein which is immunogenic to the disease.

DESCRIPTION OF THE PREFERRED EMBODIMENTS

Figure 1:
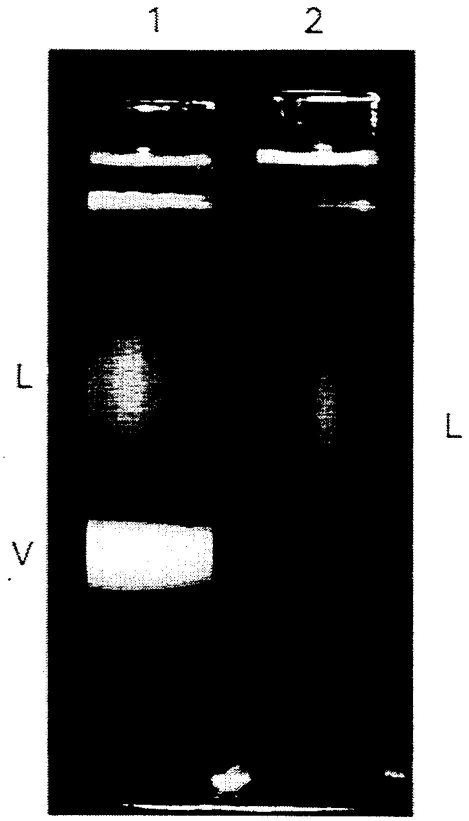
FIG. 1 is a photograph showing virus particles separated on a gradient, for wild type (1) and the mutant ts 1201 (2)

When L-particles were first identified, it was not known whether they were peculiar to HSV-1 or to the strain HSV-1 used, namely strain 17, or of more widespread occurrence. It has now been shown that these particles are also produced by a different HSV-1 strain, Strain F (Ejercito et al., 1968) and other, distantly related $\alpha$-herpesviruses, namely pseudorabies virus strain Ka (Kaplan and Vatter, 1959) and equine herpesvirus 1 strain AB4 (obtained from E. Telford, MRC Virology Unit, Institute of Virology, Glasgow G11 5JR, Scotland). The diverse nature of these viruses makes it very highly probable that L-particles will be generally obtainable from $\alpha$-type herpesviruses and from other types of herpesvirus.

The present invention makes it possible to produce L-particles substantially free of infectious virions, by using a virus which has undergone an appropriate genetic disablement. In a preferred embodiment, cells are infected with a conditional lethal mutant under non-permissive conditions. The term "conditional lethal mutant" refers to a mutant lethal to virus growth under certain conditions. Temperature is a common example of such a condition, cells being infected with a temperature-sensitive mutant, e.g. ts 1201, at a non-permissive temperature. The non-permissive temperature is any temperature at which the wild type virus grows, but the mutant does not and is usually in the 38°–40° C. range. The infected cells are incubated for a period sufficient to allow viral DNA replication to take place and late-translated proteins to be produces, thus allowing L-particles to be assembled and accumulate. The period required might be typically 20 hours or longer, but will vary according to the nature of the mutation.

Many other temperature-sensitive mutants can be produced and tested for effects similar to those described in the above-cited literature. Many mutants are "leaky", in the sense that they produce virions at some temperatures within the non-permissive temperature range. It is, therefore, necessary to optimise the temperature to mitigate contamination by virions, but this is a routine matter for those skilled in the art.

An alternative condition to temperature sensitivity which would prevent virion formation is the creation of a virus from which an essential gene has been deleted. For example, if a capsid protein were deleted from the virus genome, then such a virus could only be grown on genetically engineered cell lines which express this deleted capsid protein. Under these conditions, the cell line will provide the capsid protein essential for virion production. When the virus grown on these cell lines is used to infect cells which do not express the capsid protein, no virion production would take place. However, L-particles would be made, since capsid proteins are not an essential component of their production. Under these conditions, the deletion would be lethal to virus growth. There are other more sophisticated means of creating conditional lethal mutants and the term covers many ways of preventing virion production.

Any of the genes responsible for the formation of a full capsid can be appropriately disable, e.g. by deletion, mutation or insertion of nucleotide(s). Generally, a deletion will be preferred since its effects are more readily predictable, but many temperature-sensitive mutants already exist and it is likely that some of these will also suffice to produce L-particles substantially free of infectious virions.

HSV-1 mutant ts 1201 has a mutation in a gene UL26, which codes for a protein involved in DNA packaging. Other genes of HSV-1 which could be disabled to produce L-particles substantially free of virions comprise:

UL6, a gene encoding a late protein involved in DNA packaging. Mutations of tsN (Matz et al., 1983), tsF18 and tsF43, (Weller et al., 1987) are in this gene.

UL12, another gene encoding a protein, alkaline nuclease, involved in DNA packaging (Weller et al., 1990).

UL18, a capsid protein gene (Rixon et al., 1990).

UL19, a capsid protein gene. Mutations of tsG3 and tsG8 (Weller et al., 1987) are in this gene.

UL28, a gene encoding a protein involved in DNA packaging. A mutation of ts1203 (Addison et al., 1990) is in this gene.

UL33, another gene involved in producing a full capsid (al-Kobaisi et al., 1991).

US38, a capsid protein gene (Pertuiset et al., 1989); Rixon et all, 1990).

In virus preparations from wild type virus, the numerical ratio of L-particles to infectious virions in the L-particle band would normally be about $10^3$:1. Using a conditional lethal mutant is proposed above, this ratio would normally be at least $10^4$:1 and preferably lie within the range of $10^4$ to $10^{12}$1, typically being about $10^6$:1 for the mutant ts 1201. Such virus preparations are included in the invention.

Even a small proportion of virions is undesired in most intended uses of vaccination, so in the final commercial vaccine the L-particles might be produced by recombinant DNA technology. Thus, the entire herpesvirus genome, as one or a small number of DNA fragments and appropriately disabled to preclude virion formation, will be cloned and expressed to produce L-particles 'artificially', thus avoiding even slight contamination by virions.

Two methods for cloning HSV DNA to produce L-particles free from virions will now be mentioned by way of illustration. The first of these uses a bacteriophage cloning system (called the P1 cloning system) which allows cloning of the HSV genome as two large pieces of DNA (>50 kilobase pairs). The ability to clone such large segments of DNA is particularly advantageous since most other cloning methods only allow shorter DNA fragments to be cloned. When these large fragments are cloned using the P1 system, they will be amenable to manipulation using standard methods. The contemplated types of manipulation of the cloned DNA are those which would prevent virion assembly. They include deletion of one or more structural genes. In order to form L-particles without forming virions, it is expected that it will be sufficient to prevent the formation of a full capsid. A capsid lacking essential structural components will be unable to create virions. Thus, one example of a manipulation is deletion of a capsid protein. Alternatively, the signals located within the genome which are required for DNA packaging could be removed, again preventing production of mature virions. In order to make L-particles, these cloned DNA fragments would be transfected into mammalian cells and recently developed methods give high levels of transfection efficiency.

A second method is to insert signals from yeast DNA into the HSV genome and in this way create a 'yeast artificial chromosome' (YAC). Following transfection into yeast cells, YACs behave in the same way as normal yeast chromosomes and are therefore inherited by daughter cells after cell division. Again the HSV genome would be manipulated in such a way that only L-particles and not virions would be made. DNA made from the yeast cells containing the HSV YAC would then be transfected into mammalian cells and the production of L-particles would be assayed. The production of L-particles in a virus-free system using these particular recombinant DNA techniques is a preferred feature of the present invention.

The L-particles are defined herein as having tegument and outer envelope, but lacking capsid and viral DNA. It is expected that L-particles will be able to stimulate the immune responses elicited by virions. They will thus be able to stimulate a humoral response. Furthermore, we have demonstrated experimentally that L-particles will bind to host cells, fuse with those cells and release their contents. In this way they will assist in the acquisition of cell-mediated immunity. (The experimental demonstration involved studying the properties of two tegument proteins, namely (1) the HSV-1 or HSV-2 virion host shut-off (vhs) protein and (2) the transcriptional activator $\alpha$-TIF (Vmw 65). For these experiments, virions and L-particles were prepared from wild type HSV-1 and HSV-1 mutants. L-particles were found to be as efficient as virions in supplying these proteins in a fully functional state.

These immune responses are expected to provide protection against the type of herpesvirus from which the L-particles are derived. It is intended that the L-particles will provide protection against a herpesvirus infection of the strain which provides the relevant proteins of the L-particles, but there will doubtless, in many cases, be a degree of protection against other strains within a serotype or even against strains of a different serotype.

While the invention thus far described relates to L-particles wholly composed of elements of a single strain of herpesvirus, a wider range of protection could be provided by producing virus recombinants which would have the ability to express foreign DNA in such a way as to incorporate proteins or epitopic peptides from other viral types or other strains of herpesvirus into L-particles. For example, varicella-zoster virus DNA can be inserted in HSV-1 DNA to produce particles containing VZV proteins. Indeed, the foreign (non-native or heterologous) DNA in such constructs could be non-herpesvirus DNA encoding foreign protein(s) or peptide(s). (The term "foreign" herein means foreign to the strain of herpesvirus from which the L-particles are derived).

Where the foreign DNA is foreign only in the sense that it is derived from another strain or type of HSV, it is expected that a recombinant HSV containing the foreign DNA will express it without difficulty in most cases, so that the expressed protein becomes incorporated within the L-particles, (e.g. in the envelope or in the tegument). Thus, for example, L-particles containing a foreign protein in their structure can be prepared by co-transfecting appropriate cells with DNA comprising (1) DNA of HSV-1, preferably of a conditional lethal mutant, and (2) a plasmid containing (a) HSV-1 DNA which is inessential to viral growth (so-called non-essential region [NER]), interrupted by (b) the foreign DNA. The cells can be any appropriate to vaccine use and approved by regulatory authorities. They may be, for example, baby hamster or monkey kidney cells. The transfected cells are incubated to grow the virus, and the virus is then purified by selecting plaques and re-growing them. The viral culture is then incubated at the appropriate non-permissive condition, preferably for at least 24 hours, to produce L-particles containing foreign protein or a peptide expressed from the recombinant herpesvirus DNA, substantially free of virions. (Alternatively, wild type virus could be used and H-particles separated from L-particles, but this is not preferred). The supernatant medium is separated from the cellular material as completely as possible and provides a suspension of L-particles. The above description applies mutant mutandis to other starting herpesviruses.

Considerable interest centres on the expression of foreign DNA which is not native to HSV, e.g. of another herpesvirus such as human cytomegalovirus (HCMV) or varicella zoster virus (VZV), or of another family of viruses, e.g. the immunodeficiency virus group. It may be necessary to incorporate the foreign DNA into a region of the herpesvirus genome which will provide signals by which the protein expressed is targeted to the L-particle. This will be a matter of trial and error, but it has already been shown in Example 3 hereinafter that the virion host shut-off (vhs) protein gene of HSV-1 is capable of providing the requisite signals. Experimentation with marker genes along the lines indicated in Example 3 will readily provide appropriate locations for the construction of recombinants. The same procedure of homologous recombination, as described above, can be used to make the recombinant. In appropriate cases, the foreign DNA could instead be introduced in the herpesvirus DNA by direct ligation.

Examples of the foreign proteins and peptides which can be introduced into L-particles by procedures as described above are any HSV structural protein, or combination of structural proteins, such as gD, gB, immediate-early 183, Vmw 65, and proteins of other herpesviruses such as HCMV gB, and immunodeficiency virus proteins such as HIV-1 or HIV-2 gp 120 or gp 160.

The vaccine of the invention may be of any formulation by which L-particles can stimulate formation of antibodies to proteins of a herpesvirus. The vaccine will therefore normally contain an immunostimulant (e.g. adjuvant) or vehicle, as well as the L-particles. It can, of course, also contain other conventional additives, such as excipients. The invention includes a live L-particle vaccine, as well as a vaccine of L-particles which have been inactivated, e.g. by formaldehyde or irradiation. Particularly for a live vaccine, it is suggested that whole L-particles are used. If the vaccine is inactivated the L-particles could be used whole or possibly in a disrupted or comminuted form if it is desired to release proteins from the tegument. The vaccine is desirably made up into unit dosage forms. Appropriate doses can be derived from knowledge of the use of herpesvirus vaccines, e.g. of HSV-1 or varicella-zoster virus, but the dose will also depend on whether the L-particles are intended to protect against a herpesvirus infection or are the product of vectors by which an immunogenic foreign protein is produces. In the latter case, dosages appropriate to the foreign protein will have to be calculated.

For administration of the L-particles to the appropriate mammals, any of the conventional routes used in the viral vaccine field can be used. These will be predominantly subcutaneous or intramuscular injection, but other routes, e.g. oral, intravenal, intravaginal and intranasal, may be more appropriate on occasions. They can be administered for the prophylaxis of herpesvirus or, if foreign DNA is incorporated in the herpesvirus DNA, other diseases to which a protein or peptide expressed from the foreign DNA is immunoprotective or serves to stimulate the immune system to increase an immunoprotective effect. In particular, the invention is expected to be useful in the prophylaxis of AIDS in HIV-susceptible or HIV-positive patients.

Although the invention applies predominantly to human patients, it is also applicable, for example, to diseases in animals, e.g. to equine herpesviruses, and to the L-particles of such a virus for administration to horses.

The following Examples illustrate the invention. "FICOLL" and "PARLODION" are Registered Trade Marks.

EXAMPLE 1

This Example shows how L-particles can be obtained from a wild type virus.

METHODS

Virus Strain

HSV-1 strain 17 (Brown et al., 1973) was obtained from the Institute of Virology, University of Glasgow, Glasgow G11 5JR.

Growing and Labelling Virus Particles

Monolayers of BHK-21 C13 cells in roller bottles were infected with very low numbers of gradient-purified HSV-1 strain 17 virions (approximately 1 pfu/$10^5$ cells) suspended in 40 ml of culture medium (Eagle's medium containing 2% calf serum; Macpherson & Stoker, 1962). After incubation at 31° C. for 3 days, when most of the cells were deemed to be productively infected, the medium was replaced with 40 ml of fresh culture medium, and incubation continued for a further 48 h, by which time marked cytopathic effect was observed.

To label the viral proteins, glycoproteins and DNA, we added either L-[$^{35}$S]methionine (26 MBq/bottle), D-[2,6-$^3$H]mannose (26 MBq/bottle) or [Me-$^3$H]thymidine (26 MBq/bottle) 7 h after the medium was changed, and incubation was continued for a further 41 h.

To label the phosphoproteins, the medium was changed three days post-infection to culture medium containing only 1% of its usual concentration of phosphates and 7 h later [$^{32}$P]orthophosphate (37 MBq/bottle) was added and incubation continued for a further 41 h.

Purification of Virus Particles

The essential feature of the purification of extracellular virus particles was to maintain constant osmolarity throughout the purification by always suspending the particles in the modified medium (described below) and using osmotically inert FICOLL for gradient centrifugation.

Thus, after 5 days of incubation the media from four roller bottles were combined, cell debris was removed by low speed centrifugation (1000 g for 30 min at 4° C.), and the virus particles in the clarified medium were pelleted by centrifugation (23000 g for 2 h at 4° C.). Then the pellet was gently resuspended in 1 ml of modified medium (culture medium without phenol red and calf serum) and layered on a 35 ml preformed gradient of 5 to 15% FICOLL 400 (Sigma) suspended in this medium. After centrifugation using a swing-out rotor (26000 g for 2 h at 4° C.) the two well separated particle bands were individually withdrawn by side punctures. Finally the particles constituting these bands were pelleted by centrifugation (80000 g for 2 h at 4° C.), gently resuspended in 200 μl modified medium and either used immediately or stored at −70° C.

Analysis of Virus Particles

The amounts of radioactively labelled materials in the particles were estimated by scintillation spectrophotometry using 2 μl samples from the 200 μl final suspensions.

The amount of protein in the particles were determined by the method of Lowry et al., (1951) using bovine serum albumin as a standard.

Titration of Virus Particles

Serial dilutions of the virus particles were made with the modified medium. Monolayers of BHK-21 C13 cells (in 35 mm Petri dishes) were infected with 1 ml aliquots of the serially diluted particles and after 1 h incubation at 31° C. the inoculum was removed, 3 ml of solid overlay medium (culture medium without phenol red but containing 2.8% calf serum and 0.625% agarose; agarose type HSA, Park Scientific) was added and after solidification of the medium at room temperature (approximately 1 h) the dishes were incubated at 31° C. for 4 days. Finally the cultures were fixed with Cidex (4 h at room temperature) and then stained with Giemsa stain.

Particle Counts

Virus suspensions were mixed with equal volumes of a 1% solution of sodium silicotungstate and a suspension of latex beads ($1.42\times10^{11}$ particles/ml). A droplet of this suspension was placed on an electron microscope grid and after 5 min, to allow the particles to settle, the excess suspension was removed and the particles were counted under the electron microscope.

Electron Microscopy of Particles

Virus particles were fixed by mixing suspensions with equal volumes of an 8% formaldehyde solution (freshly made up in the modified medium) and leaving them at room temperature for 10 min. The fixed particles were then negatively stained (the areas around the particles become dark) by the addition of equal volumes of 1% sodium silicotungstate and examined under the electron microscope.

PAGE Analysis of Polypeptides

Discontinuous SDS-polyacrylamide slab gels cross-linked with diallyltartardiamide (DATD) were used as described by Ongrádi et al., (1985). The separating gels contained 10, 12, 15 or 18% polyacrylamide, and the ratio of polyacrylamide to DATD was 100:1.75.

The assignment of $M_r$ values to individual polypeptides was based on their positions in the gels in relation to the positions of major polypeptides with well established $M_r$s (Vmw273, Vmw155, Vmw82/81, Vmw65 and Vmw37). These $M_r$s were in good agreement with those derived from standard markers ([$^{14}$C]methylated protein mixtures; CAF.626 and CFA.645; Amersham) which were included in every gel.

RESULTS

Separation of the H and L Particles

During the purification of HSV-1, FICOLL gradient centrifugation separated a diffuse upper band and a sharp, well defined lower band. The positions of the bands suggested significant differences in the densities of the particles in these bands and for this reason they were designated light (L) and heavy (H).

The particles from the two bands were withdrawn and re-centrifuged separately in order to study their sedimentation characteristics. The sharpness of the lower band suggested that the H particles constituting this band were homogeneous. The L particles from the upper band also migrated as a well defined, although wider band, indicating that these particles were distinct, but less homogeneous than the H particles.

Electron Microscopy

The particles were fixed with formaldehyde to preserve their structural integrity and then negative-stained with sodium silicotungstate.

The H particles could be clearly identified as typical HSV virions, since they consist of an outer membrane with clearly visible spikes on the outer surface, an icosahedral nucleocapsid and the electron-dense tegument between the membrane and the nucleocapsid.

The L-particles appeared to be virus-like entities without a nucleocapsid since they consist of an outer membrane (with surface spikes) enclosing uniform granular material with no discernible internal structure. They were not as regular in size as virions, which may explain why they formed a wider band in the FICOLL gradient. Virions were only occasionally observed in the L-particle preparation.

Further Characterisation

TABLE

Chemical composition and infectivity of the H and L particles

| | Particles* | |
|---|---|---|
| | H | L |
| Protein [$^{35}$S]methionine (cpm/μl) | 56 600 | 75 300 |
| Lowry method (mg/ml) | 5.1 | 6.2 |
| Infectivity (pfu/ml) | $5 \times 10^9$ | $4 \times 10^6$ |
| Particle count (particles/ml) | $1.15 \times 10^{11}$ | $8 \times 10^{10}$ |
| Infectivity to particle ratio | 1:23 | 1:20,000 |
| DNA [$^3$H]thymidine (cpm/μl) | 125 000 | 472 |

Analysis of the purified [$^{35}$S]methionine-labelled particles by scintillation spectrophotometry and the Lowry method suggested that approximately similar quantities of virions and L particles were produced during infection and this was confirmed by particle counts (Table).

Scintillation spectrophotometric analysis of [$^3$H]thymidine-labelled particles confirmed that the virions (H particles) contained the genomic DNA and suggested that the L particles did not; the small amount of DNA associated with the L particles almost certainly resulted from 0.1 to 0.5% cross-contamination with H particles, see the Table above.

The infectivity to particle ratio of the H particles confirmed that they are infectious virions, while the much lower ratio associated with the L particles originating from the same infected cell population suggested that L particles were not infectious but merely contaminated with low levels (about 0.1%) of virions.

Thus these results indicate that the culture medium of HSV-1 infected cells following virus replication contains similar amounts of the two types of particles, H particles which are the familiar infectious HSV virions, and L particles which clearly represent a new type of HSV-specified entity that contains neither capsid nor viral DNA and is not infectious.

Polypeptide Composition

The polypeptide compositions of [$^{35}$S]methionine-labelled H and L particles were analysed by electrophoresis using 10%, 12%, 15% and 18% polyacrylamide gel crosslinked with DATD.

The polypeptide profiles of H and L particles on a 10% polyacrylamide gel showed that the most significant polypeptides common to both particles were the 273K, 82/81K, 65K and 40K polypeptides, and two diffuse areas of overlapping bands with approximate $M_r$s of 134K to 123K and 63K to 60K. Several other polypeptides (115K, 108K, 69K, 46K 44K and 42K) were also observed in both particles.

The H particles also contained several polypeptides which were apparently absent from the L particles, namely two of the major capsid proteins (155K and 37K and polypeptides of 143K, 104K, 86K, 56K, 54K and 50K). They also contained more of the 69K polypeptide than the L-particles, indicating either that larger amounts of this polypeptide are incorporated into the H particles, or that one or more polypeptides unique to this particle comigrate with the 69K polypeptide.

The L particles contained at least three additional polypeptides (175K, 92K and 55K) which were either absent from or present in much lower quantities in the H particles. These are presumably tegument or membrane-associated proteins. The 175K phosphoprotein has been shown to be the immediate early regulatory protein Vmw 175. Three of the unique polypeptides of the H particles (155K, 53K and 37K) are at present known to be components of the capsid.

Phosphoproteins

Particles were labelled with [$^{32}$P]orthophosphate and analysed by PAGE.

Using a 10% gel, polypeptides 273K, 82/81K, 65K and 40K were shown to be phosphorylated in both types of particle preparation. In addition, the three polypeptides of the L particle (175K, 92K double band and 55K) were also phosphorylated. These particles also contained two phosphorylated polypeptides of 134K and 60K. Trace amounts of these two phosphopolypeptides were also observed in the preparation of H particles.

Additional description, photographs etc. are available in the corresponding literature paper, Szilágyi and Cunningham (1991).

As far as it is known, this is the first description of a light particle in the sense defined above. Although Irmiere & Gibson (1983) recovered a light non-infectious enveloped particle from the culture medium of tissue culture cells infected with human strains of cytomegalovirus, this particle differs from the L particle of HSV-1 since, although it lacks viral DNA, it possesses a capsid structure and some form of core. L-particles have neither capsid nor core.

EXAMPLE 2

This Example shows how L-particles can be obtained from a mutant virus, without being accompanied by significant production of infectious virions.

METHODS

Preparation of a Temperature-sensitive Mutant of Herpes Simplex Virus Type I, Designated ts 1201

A mutant 17tsJC116 was isolated following UV-mutagenesis of HSV-1 strain 17 by Coates (1982). An EcoRI F fragment from a clone of DNA from this mutant was recombined into HSV-1 strain 17 wild type (WT) virus to produce mutant ts 1201. (Preston et al., 1983).

Identification of a Mutation

A BamHI/SalI fragment containing the ts 1201 mutation was sequenced and a single base-pair change from the wild type DNA sequence was identified. The change was from an A residue to a T residue at position 50897 on the sequence of McGeoch et al., (1988). This change results in the substitution of a tyrosine with a phenylalanine in the amino acid sequence of the UL26 protein (Al-Kobaisi, 1989).

Patent Deposit of ts 1201

While it is likely that this mutation is sufficient to produce the requisite genomic change to prevent capsid formation and thus generate L-particles, and therefore that the L-particles of this mutant of HSV-1 can be produced by recombinant DNA means, ts 1201 has been deposited, purely by way of precaution, to ensure that the invention can be even more readily carried out. The deposit is under the Budapest Treaty on the deposit of micro-organisms for the purposes of patent procedure at the European Collection of Animal Cell Cultures, PHLS Centre for Applied Microbiology and Research, Porton Down, Salisbury, Wiltshire SP4 OJG, England on Jun. 20, 1991 under Accession No. V91062004.

Growth of Viruses and Purification of Virions

BHK C13 cells were grown as described previously (Rixon and McLauchlan, 1990). Stocks of HSV-1 strain 17 and ts 1201 were obtained by infecting 10 roller bottles of cells at a moi of 1/300 pfu per cell. Following infection at 31° C. for 4 days, virus was harvested and purified on 5–15% FICOLL gradients as described previously in Example 1 above. Bands were collected by side puncture, diluted with Eagle's medium lacking phenol red and pelletted by centrifugation at 21,000 rpm in a Sorvall Tst41 rotor for 2 h at 4° C. Pellets were resuspended in Eagle's medium lacking phenol red and stored at −70° C.

Titration of Purified Virions

Purified virion preparations of WT and ts 1201 were titred at 31° C. (permissive) and 38.5° C. (non-permissive temperature for ts 1201) and their particle/pfu ratios were determined at 31° C. to be of the same order of magnitude. Titration of the ts 1201 virion stock confirmed that it was temperature-sensitive under the conditions used, with a reduction in titre over WT of greater than $10^5$.

Electron Microscopy

Cells to be used for electron microscopy were grown in 30 mm petri dishes containing a 13 mm glass coverslip. At appropriate times after infection the cells were washed with phosphate buffered saline (PBS) and fixed with 2.5% glutaraldehyde in PBS for 1 h at 4° C. Cells were then washed in PBS and osmium tetroxide (1% in PBS) was added for 1 h.

Replica Formation

The coverslips were removed to a 24 well tissue culture tray, dehydrated through a graded alcohol series and dried in a critical point drier. The coverslips were shadowed with Pt/Pd for 7 s at an angle of 75° in a Balzers shadowing unit, then rotary shadowed with carbon to provide additional support. The shadowed surface was overlayed with 50 μl of 0.25% PARLODION amyl acetate and allowed to dry. Each coverslip was broken in half and the shadowed surface was scored into approximately 2 mm squares. To release replicas, the coverslips were floated on hydrofluoric acid until they dissolved. The replica squares were picked up on a Pt wire hoop and washed on distilled water. Cell material was removed by floating replicas on 66% chromic acid for 1 h. Clean replicas were washed 3 times on water, then dried onto 400 mesh copper microscope grids. When dry, the PARLODION support film was removed by immersing the grids in amyl acetate and the replicas were examined in a JEOL 100S electron microscope.

Thin Sectioning

The remaining cells on each 30 mm petri dish were harvested, pelleted in BEEM capsules, dehydrated and embedded in Epon 812 resin as described previously (Preston et al., 1983). 130 nm thick sections were cut and stained with uranyl acetate and lead citrate.

Polyacrylamide Gel Electrophoresis

Proteins were separated on a 5–12% gradient polyacrylamide gel which had been crosslinked with 5% N,N'-methylene bisacrylamide, using the buffer system described by Laemmli (1970). Proteins were visualised by silver staining as described by McLean et al., (1990).

Production of L-particles

Five roller bottles of cells were infected with either gradient-purified ts 1201 or WT virus. Following incubation at 38.5° C. for 24 h, particulate matter present in the supernatant media was pelletted, resuspended and banded on 5–15% FICOLL gradients as described in Example 1.

RESULTS

A. Sampling

Cells were grown on 30 mm petri dishes with each contained a 13 mm glass cover slip. Following infection with 5 pfu/cell of either WT virus or ts 1201, cells were incubated at 38.5° C. A portion of each inoculum was retained for subsequent titration (these constituted the zero hour samples). At 1 h after infection, the input inocula were removed and were also retained (these constituted the 1 hour samples). The cells were washed with ETC10 and incubation was continued at 38.5° C. At 6, 10 and 24 h, supernatant medium was collected from each plate and retained for titration. The cells from each time point were used for formation of surface replicas, while the remaining cells on the dish were prepared for thin sectioning.

B. Virus Growth

As expected, the WT virus, after an initial decline in titre during the eclipse phase, showed a rapid increase in virus production to a level about 10-fold higher than the input virus. By contrast, ts 1201 titres declined throughout the period of infection to about 100-fold below that of the input virus, thereby confirming that the ts 1201 used in this experiment was behaving in a fashion typical of this mutant. This ensured that the results obtained from the ts 1201-infected cells were not a result of leak or reversion of the mutant.

C. Appearance of Particles on the Cell Surface

Examination of replicas prepared from WT-infected cells revealed a characteristic series of changes to the cell surface. At 1 h the cell surface was smooth and showed no evidence of infection compared with mock-infected samples. By 6 h, many cells had small numbers of approximately 250 nm diameter particles on their surfaces and by 10 h large numbers of these particles had accumulated on most cells. The sizes of these particles were consistent with those of virions. At 24 h the cells were decidedly rounded and had dense coverings of particles. The distribution of these particles on the cell surface was frequently assymetric with marked concentrations over the area of the nucleus and around regions at the periphery of the cell being typical.

Examination of ts 1201-infected cells revealed a very similar pattern of changes. Thus at 1 h after infection their surfaces were indistinguishable from those of mock-infected cells apart from the presence of occasional particles which presumably were derived from the inoculum. By 6 h, small numbers of particles were present on the cell surfaces and their number had increased at 10 h and 24 h. The distribution and abundance of particles were comparable to those found with WT virus but they appeared slightly less uniform in size.

D. Nature of the Particles on the Cell Surface

To determine the nature of the particles present on the surfaces of infected cells, thin sections prepared from the remainder of each sample were examined. Both virions and particles lacking obvious capsids, which we consider to be L-particles, were present on WT-infected cells. Similar particles were also found with virions in intracellular vacuoles.

Thin sections of ts 1201-infected cells demonstrated the phenotype typical of this mutant (Preston et al., 1983). Thus, the nuclei contained aggregations of characteristically large cored capsids which lacked DNA. Full, DNA-containing, capsids were not apparent and there was no evidence of mature virions either in the cytoplasm or on the cell surface. The particles that were present on the surface lacked capsids and closely resembled L-particles in appearance. Particles of a similar type were also frequently seen in cytoplasmic vacuoles. A number of features were also seen which could be considered as L-particles in the process of formation by budding into vacuoles. However, due to the lack of diagnostic capsid, it was impossible to be dogmatic as to the nature of these features.

Identification and Protein Composition of Particles Released from ts 1201-Infected Cells Referring to FIG. 1 of the drawings, the photograph shows bands of pelleted particulate material separated on the gradient, with bands L ascribed to light particles and V to virions. Tube 1 contains the wild type and 2 the mutant. The gradient containing the WT virus preparation (FIG. 1, lane 1) had two bands which correspond to those described in Example 1: a sharp lower band of virions and a diffuse upper band of L-particles. By contrast, the virion band could not be observed in the ts 1201 gradient (FIG. 1, lane 2). However, a diffuse band was present which co-migrated with, and was of a similar intensity to, the L-particle band present in the WT virus preparation. When collected and examined by negative staining, this band was shown to contain material which appeared identical to typical L-particles.

Figure 2:
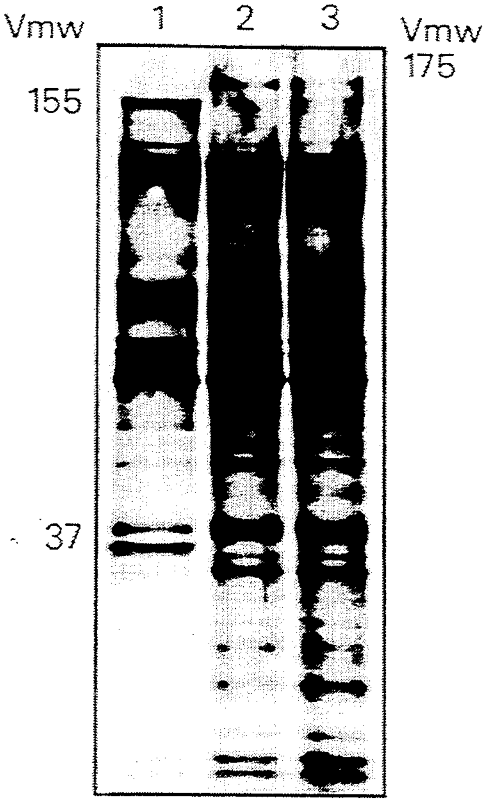
FIG. 2 is a photograph of a silver-stained polyacrylamide gel showing polypeptide bands obtained by PAGE from the gradient- separated viral particles.

Analysis of the polypeptide composition of the gradient-banded material by PAGE confirmed the above assignment. Referring to FIG. 2 of the drawings, lanes 1 and 2 show the polypeptide profiles of virions and L-particles, respectively, from the WT virus, while lane 3 shows the composition of the particles produced by ts-1201 at the non-permissive temperature. The positions of bands for HSV-encoded proteins Vmw 175 (diagnostic of L-particles) and Wmw 37 and 155 (diagnostic of virions) are shown. (The Vmw numbers indicate relative molecular masses in kiloDaltons). The compositions of the WT virions and L-particles conformed to the previously described patterns (Example 1). Thus, Vmw 155 (Mr 155000) and Vmw 37 (Mr 37000) capsid proteins, which were abundant in virions, were greatly reduced in L-particles, while Vmw175 was apparent only in L-particles. The protein profile of the ts 1201 band was virtually indistinguishible from that of the WT L-particles and the diagnostic Vmw175 band was clearly visible (FIG. 2, lane 3). Interestingly, despite the very low levels of infectious virions in this band, the Vmw 155 (Mr 155000) capsid protein was present in quantities similar to those found in WT L-particles.

PREPARATION OF A VACCINE

Although virions are still produced at low levels by ts 1201- infected cells, the numerical ratio of L-particles to virions is typically about $10^6$:1, compared with about $10^3$:1 in WT virion preparations. For this preparation of a vaccine it will be advisable to remove all residual possibility of herpesvirus infection. This can be done by inactivating the preparation, e.g. with formaldehyde or by UV irradiation. A dose of 160 $mJ/cm^2$ of UV light of wavelength 254 nm delivered by a UV Stratalinker Model 180 would normally suffice and probably this dose could be lowered. However, the possibility of using a live vaccine is not excluded, since it is likely that methods of further purifying the L-particles will soon be devised.

EXAMPLE 3

This Example demonstrates incorporation of a foreign gene into HSV-1 and expressing it to produce foreign protein as part of a fusion protein in L-particles. Thus, the L-particles are here serving as a vector. In this Example, we have linked the polypeptide coding sequences of a structural component of the virus (in this case a protein called the virion host shut-off protein, abbreviated to vhs) encoded by gene UL41 to those of a non-structural marker protein (a bacterial enzyme called chloramphenicol acetyltransferase, CAT for short). We have then inserted this chimeric gene into the virus genome and looked for the presence of a vhs-CAT fusion protein in virions and L-particles.

Figure 3:
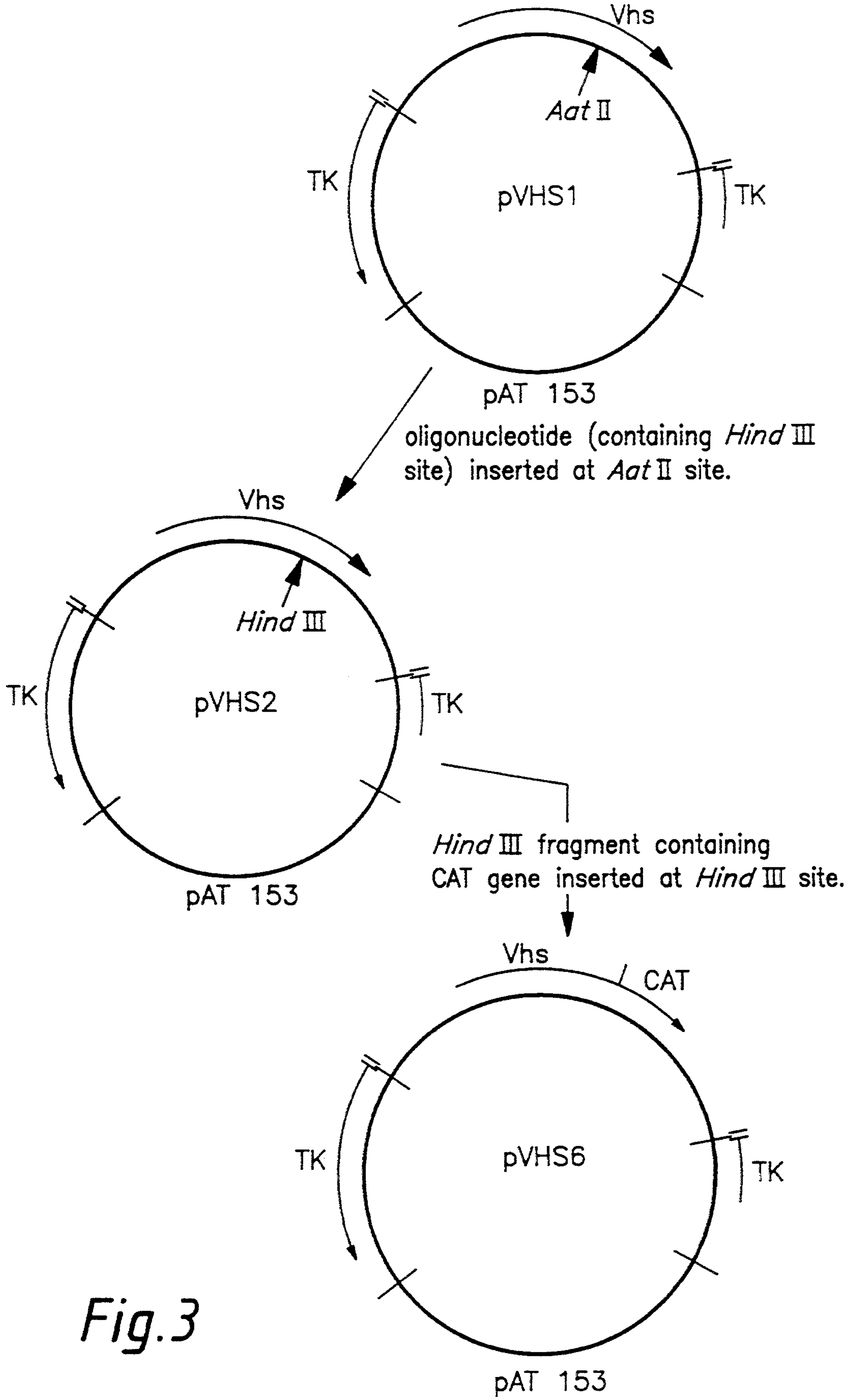
FIG. 3 is a plasmid diagram showing the derivation of a plasmid carrying foreign DNA for insertion into herpesvirus DNA, for preparing L-particles incorporating a foreign protein (see Example 3).

The plasmid which was used as the basis for constructing a vhs-CAT fusion gene was pMF1. pMF1 consists of a 3.7 kb fragment containing the vhs gene from HSV-2 strain G inserted into a plasmid, pTK1 that contained the thymidine kinase (TK) gene from HSV-1 strain 17 inserted into the well known pAT 153 plasmid. This 3.7 kb fragment was inserted into the TK sequence in pTK1 in such a way as to inactivate the TK enzyme. In order to link the CAT coding sequences to the HSV-2 vhs coding sequences, the following strategy (illustrated schematically in FIG. 3) was employed:

1) pMF1 contains a unique HindIII restriction enzyme site and this was removed from the plasmid by standard gene manipulation procedures. Thus the resultant plasmid (called pVHS1) did not contain any HindIII sites.
2) An AatII restriction enzyme site is located just upstream from the 3′ end of the vhs protein coding sequences. A synthetic oligonucleotide was inserted at this AatII site in pVHS1 to create pVHS2. The oligonucleotide has two essential features. Firstly, it contains the sequences between the AatII site and the 3′ end of the vhs open reading frame (ORF), which are present in pVHS1, and hence it will regenerate the complete ORF. Secondly, a HindIII site is present immediately after the codon specifying the C-terminal amino acid of vhs. This HindIII site was incorporated into the oligonucleotide in such a way that the CAT coding sequences inserted at this site (see step 3) would be in the same reading frame as the vhs gene.
3) A HindIII fragment from a plasmid pCAT1 carrying the CAT coding sequences was then inserted into the HindIII site in pVHS2 to generate plasmid pVHS6. Thus, the vhs gene in pVHS6 was intact and in-frame with the coding sequences for CAT.

To insert this vhs-CAT chimeric gene into the virus genome, pVHS6 was recombined with VHS-1 strain 17 DNA in tissue culture cells. Since the DNA fragment carrying the vhs-CAT fusion was inserted into the HSV-1 TK polypeptide coding sequence, the incorporation of the vhs-CAT sequences into the virus genome should inactivate the endogenous virus TK gene, resulting in the creation of a TK minus virus. Such viruses can be preferentially selected by growing the virus population generated from the recombination procedure in the presence of bromodeoxycytidine (BCdR). Therefore, after the recombination had been performed, the resultant pool of viruses was grown twice in the presence of BCdR and thereafter plaques from individual viruses were picked and grown. These procedures, including the TK- selection, are standard methods for producing and purifying recombinant viruses. One of the individual plaques which had been picked and grown was shown to contain CAT DNA sequences that had been inserted in the TK gene in the virus DNA. A large scale preparation of this virus was grown and called vhs-CAT. The virus preparation was banded on Ficoll gradients and virions and L-particles were purified as in Example 1. The proteins present in the virions and L-particles were separated on a 7.5% polyacrylamide gel alongside a L-particle preparation from a wild-type virus which did not contain any CAT sequences. After transfer to a nitrocellulose membrane, the membrane was probed for the presence of the vhs-CAT fusion protein with an antibody to CAT. This antibody is made by 5 Prime→3 Prime Inc., 5603 Arapahoe, Boulder, Colo. CO 80303, USA. An autoradiograph showed that this antibody detected a protein of approximately 85,000 to 90,000 molecular weight in the vhs-CAT virions and L-particles but not in the CAT minus, wild-type virus. The size of this protein fits with the predicted size of the vhs-CAT fusion polypeptide (vhs gene ORF 492 codons=59 kDa; CAT gene ORF 219 codons=24 kDa; linker between vhs and CAT gene ORFs 14 codons=1.6 kDa; total=85 kDa approximately). An additional band appeared only in the vhs-CAT virion sample at a position indicating a m.w. of about 155,000. This is ascribed to a cross-reaction between the CAT antibody and the major capsid protein Vmw 155 present in virions, but not in L-particles, and as such is not significant.

In addition, extracts from cells infected with vhs-CAT and from purified vhs-CAT virions and L-particles were tested for CAT activity in a simple assay. The results show that the vhs-CAT fusion protein retains CAT activity. To date, therefore, preliminary analyses of the vhs-CAT virus have revealed that the vhs-CAT fusion protein is incorporated into virions and L-particles and the CAT portion of the protein remains enzymically active. This shows that it is possible to insert heterologous, non-structural proteins into virions and L-particles by linking them to known structural genes.

CAT was chosen as an appropriate gene for these studies since it is easily detected and is a bacterial gene with no counterpart in animal cells. However, similar procedures could be used to introduce other proteins, including those significant for vaccine purposes, into L-particles.

REFERENCES

ADDISON, C., RIXON, F. J. and PRESTON, V. G. (1990). Herpes simplex virus type 1 UL28 gene product is important for the formation of mature capsids. J. Gen. Virol. 71, 2377–2384.

AL-KOBAISI, M. F. (1989). Identification and characterisation of herpes simplex virus genes required for encapsidation of DNA. PhD thesis, Glasgow University.

AL-KOBAISI, M. F., RIXON, F. J., McDOUGALL, I. and PRESTON, V. G. (1991). The herpes simplex virus UL33 gene product is required for assembly of full capsids. Virology 180, 380–388.

BROWN, S. M., RITCHIE, D. A. and SUBAK-SHARPE, J. H. (1973). Genetic studies with herpes simplex virus type 1. The isolation of temperature-sensitive mutants, their arrangement into complementation groups and recombination analysis leading to a linkage map. J. Gen. Virol. 18, 329–346.

COATES, J. A. V. (1982). Genetic and biochemical studies with temperature-sensitive mutants of herpes simplex virus type 1. PhD thesis, Glasgow University.

DARGAN, D. J. (1986). The structure and assembly of herpesviruses. In Electron Microscopy of Proteins, vol. 5, Virus Structure, pp. 359–437. Edited by J. R. Harris and R. W. Horne. London: Academic Press.

EJERCITO, P. M., KIEFF, E. D. and ROIZMAN, B. (1968). Characterisation of herpes simplex virus strains differing in their effect on social behaviour of infected cells. J. Gen. Virol. 2, 357–364.

IRMIERE, A. and GIBSON, W. (1983). Isolation and characterisation of a non-infectious virion-like particle released from cells infected with human strains of cytomegalovirus. Virology 130, 188–133.

KAPLAN, A. S. and VATTER, A. E. (1959). A comparison of herpes simplex and pseudorabies viruses. Virology 7, 394–407.

LAEMMLI, U. K. (1970). Cleavage of structural proteins during the assembly of the head of bacteriophage T4. Nature, London 227, 680–685.

LOWRY, O. H., ROSEBROUGH, N. J., FARR, A. L. and RANDALL, R. J., (1951). Protein measurement with the Folin phenol reagent. J. Biol. Chem. 193, 265–275.

MATZ, B., SUBAK-SHARPE, J. H. and PRESTON, V. G. (1983). Physical mapping of temperature-sensitive mutations of herpes simplex virus type 1 using cloned restriction endonuclease fragments. J. Gen. Virol. 64, 2261–2270.

MCGEOCH, D. J., DALRYMPLE, M. A., DAVISON, A. J., DOLAN, A., FRAME, M. C., MCNAB, D., PERRY, L. J., SCOTT, J. E., and TAYLOR, P. (1988). The complete DNA sequence of the long unique region in the genome of herpes simplex virus type 1. J. Gen. Virol. 69, 1531–1574.

McLEAN, G., RIXON, F. J., LANGELAND, N., HAARR, L., and MARSDEN, H. (1990). Identification and characterisation of the virion protein products of herpes simplex virus type 1 gene UL47. J. Gen. Virol., 71, 2953–2960.

ONGRÁDI, J., CUNNINGHAM, C. and SZILÁGYI, J. F. (1985). The role of polypeptides L and NS in the transcription process of vesicular stomatitus virus New Jersey using the temperature-sensitive mutant tsE1. J. Gen. Virol. 66, 1011–1023.

PERTUISET, B., BOCCARA, M., CEBRIAN, J., BERTHELOT, N., CHOUSTERMAN, S., PUVION-DUTILLEUL, F., SISMAN, J. and SHELDRICK, P. (1989). Physical mapping and nucleotide sequence of a herpes simplex virus type 1 gene required for capsid assembly. J. Virol. 63, 2169–2179.

PRESTON, V. G., COATES, J. A. V., and RIXON, F. J. (1983). Identification and characterisation of a herpes simplex virus gene product required for encapisidation of virus DNA. J. Virol, 45, 1056–1064.

PRESTON, V. G., RIXON, F. J., McDOUGALL, I. M., McGREGOR, M. and AL KOBAISI, M. F. (1992). Processing of the Herpes Simplex Virus assembly protein ICP 35 near its carboxy terminal end requires the product of the whole of the UL26 reading frame. Virology 186, 87–92.

RIXON, F. J., DAVISON, M. D. and DAVISON, A. J. (1990). Identification of the genes encoding two capsid proteins of herpes simplex virus type 1 by direct amino acid sequencing. J. Gen. Virol. 71, 1211–1214.

SZILÁGYI, J. F. and CUNNINGHAM, C. (1991). Identification and characterisation of a novel non-infectious herpes simplex virus-related particle. J. Gen. Virol., 72, 661–668. Publication date: Mar. 1, 1991.

WELLER, S. K., CARMICHAEL, E. P., ASCHMAN, D. P., GOLDSTEIN, D. J. and SCHAFFER, P. A. (1987). Genetic and phenotypic characterisation of mutants in four essential genes that map to the left half of HSV-1 $U_L$ DNA. Virology 161, 198–210.

WELLER, S. K., SEGHATOLESLAMI, M. R., SHAO, L., ROWSE, D. and CARMICHAEL, E. P. (1990). The herpes simplex virus type 1 alkaline nuclease is not essential for viral DNA synthesis: isolation and characterisation of a lacZ insertion mutant. J. Gen. Virol. 71, 2941–2952.

We claim:

1. Isolated non-infectious, light (L)-particles of a herpesvirus, said particles being lighter than virions and comprising tegument surrounded by an envelope, but which lack a capsid and the viral DNA within the capsid.

2. L-particles according to claim 1 wherein the virus is herpes simplex virus (HSV).

3. L-particles according to claim 2 wherein the virus is herpes simplex virus-1 (HSV-1).

4. L-particles according to claim 1 of a herpesvirus conditional lethal mutant which under conditions non-permissive for viral growth, is able to make viral DNA and late proteins, but is unable to assemble infectious virions.

5. L-particles according to claim 4 wherein the conditional lethal mutant is a temperature-sensitive mutant and the conditions non-permissive for viral growth comprise a temperature condition.

6. L-particles according to claim 5 wherein the virus is a herpes simplex virus.

7. L-particles according to claim 6 wherein the virus is HSV-1.

8. L-particles according to claim 7 wherein the virus is HSV-1 ts 1201, deposited under the provisions of the Budapest Treaty on the deposit of micro-organisms for the purposes of patent procedure at the European Collection of Animal Cell Cultures, PHLS Centre for Applied Microbiology and Research, Porton Down, Salisbury, Wiltshire SP4 OJG, England on Jun. 20, 1991 under Accession No. V91062004.

9. A virus preparation comprising light (L-) particles of a herpesvirus, said particles being lighter than virions and lacking a capsid, and said preparation being substantially free of virions.

10. A virus preparation according to claim 9 wherein the numerical ratio of L-particles to infectious virions is at least $10^{4}1$.

11. A virus preparation according to claim 9, wherein the L-particles are of a conditional lethal mutant which under conditions non-permissive for viral growth is able to make viral DNA and late proteins but is unable to assemble infectious virions.

12. A virus preparation according to claim 10, wherein the herpesvirus is of a conditional lethal mutant which under conditions non-permissive for viral growth, is able to make viral DNA and late proteins, but is unable to assemble infectious virions.

13. A virus preparation according to claim 9 which is in an inactivated form.

14. A virus preparation according to claim 11 which is in inactivated form.

15. A vaccine comprising an immunostimulant or vehicle and L-particles according to claim 1.

16. A vaccine comprising an immunostimulant or vehicle and a virus preparation according to claim 14.

17. A method of vaccination against a disease of a mammal, which comprises administering to said mammal an immunologically effective amount of non-infectious L-particles of a herpesvirus, said particles being lighter than virions and containing a peptide or protein which is immunogenic to the disease.

* * * * *